(12) United States Patent
Josse et al.

(10) Patent No.: US 12,349,890 B2
(45) Date of Patent: Jul. 8, 2025

(54) SURGICAL SYSTEM AND METHOD

(71) Applicant: Warsaw Orthopedic, Inc., Warsaw, IN (US)

(72) Inventors: Loïc Josse, Collierville, TN (US); Jerome Nayet, St Genis Pouilly (FR); Bertrand Peultier, Les Hopitaux Neufs (FR)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 419 days.

(21) Appl. No.: 17/795,152

(22) PCT Filed: Apr. 9, 2020

(86) PCT No.: PCT/US2020/027533
§ 371 (c)(1),
(2) Date: Jul. 25, 2022

(87) PCT Pub. No.: WO2021/206723
PCT Pub. Date: Oct. 14, 2021

(65) Prior Publication Data
US 2023/0059813 A1    Feb. 23, 2023

(51) Int. Cl.
*A61B 17/02* (2006.01)
*A61B 17/70* (2006.01)

(52) U.S. Cl.
CPC ........ *A61B 17/025* (2013.01); *A61B 17/0206* (2013.01); *A61B 17/708* (2013.01); *A61B 2017/0256* (2013.01)

(58) Field of Classification Search
CPC ... A61B 17/02; A61B 17/025; A61B 17/0206; A61B 17/70; A61B 17/708
See application file for complete search history.

(56) References Cited

U.S. PATENT DOCUMENTS

| | | |
|---|---|---|
| 6,030,402 A | 2/2000 | Thompson et al. |
| 6,139,493 A | 10/2000 | Koros et al. |
| 8,974,497 B2 | 3/2015 | Cho et al. |
| 9,402,660 B2 | 8/2016 | Brinkman et al. |
| 10,314,620 B2 | 6/2019 | Cho et al. |

(Continued)

FOREIGN PATENT DOCUMENTS

| | | |
|---|---|---|
| CN | 101489497 | 7/2009 |
| CN | 108498152 | 9/2018 |

(Continued)

OTHER PUBLICATIONS

European Search Report. European Appl No. 20930065.6. Mar. 13, 2024.

(Continued)

*Primary Examiner* — Christopher J Beccia
(74) *Attorney, Agent, or Firm* — Sheridan Ross P.C.

(57) ABSTRACT

A surgical instrument includes a member connectable with a longitudinal element of a surgical distractor connected with vertebrae. At least one blade is connected with the member adjacent to an axis oriented transverse to the longitudinal element and being movable to space tissue adjacent the vertebrae. The at least one blade being intra-operatively translatable relative to the member along the axis. Surgical systems, constructs, implants and methods are disclosed.

19 Claims, 12 Drawing Sheets

(56) References Cited

U.S. PATENT DOCUMENTS

| | | | |
|---|---|---|---|
| 11,576,727 | B2 | 2/2023 | Turner et al. |
| 2006/0084844 | A1 | 4/2006 | Nehls |
| 2007/0208227 | A1 | 9/2007 | Smith et al. |
| 2008/0140129 | A1 | 6/2008 | Dalton |
| 2010/0069976 | A1 | 3/2010 | de Villiers et al. |
| 2012/0296172 | A1 | 11/2012 | Raven, III et al. |
| 2012/0316609 | A1 | 12/2012 | Wall et al. |
| 2013/0310942 | A1 | 11/2013 | Abdou |
| 2014/0024900 | A1 | 1/2014 | Capote et al. |
| 2014/0066718 | A1 | 3/2014 | Fiechter et al. |
| 2014/0107656 | A1 | 4/2014 | Masson et al. |
| 2014/0257044 | A1 | 9/2014 | Blain et al. |
| 2014/0257312 | A1 | 9/2014 | Solitario, Jr. et al. |
| 2014/0350347 | A1 | 11/2014 | Karpowicz et al. |
| 2015/0045834 | A1 | 2/2015 | McBride |
| 2015/0164569 | A1 | 6/2015 | Reitblat et al. |
| 2015/0351738 | A1 | 12/2015 | Perrow |
| 2016/0074029 | A1* | 3/2016 | O'Connell ............ A61B 17/02 600/215 |
| 2016/0089188 | A1 | 3/2016 | McBride, Jr. et al. |
| 2016/0166335 | A1 | 6/2016 | Roger et al. |
| 2016/0206442 | A1 | 7/2016 | Dvorak et al. |
| 2016/0345952 | A1 | 12/2016 | Kucharzyk et al. |
| 2017/0035406 | A1 | 2/2017 | Abidin et al. |
| 2017/0100116 | A1 | 4/2017 | Erramilli et al. |
| 2017/0112539 | A1 | 4/2017 | Hayes |
| 2017/0119449 | A1 | 5/2017 | Jones et al. |
| 2017/0215856 | A1 | 8/2017 | Martinelli et al. |
| 2017/0252107 | A1 | 9/2017 | Jones et al. |
| 2017/0258502 | A1 | 9/2017 | Abdou |
| 2017/0311985 | A1 | 11/2017 | Bobbitt et al. |
| 2018/0042594 | A1 | 2/2018 | Miles et al. |
| 2018/0161101 | A1 | 6/2018 | Barsoum et al. |
| 2018/0289363 | A1 | 10/2018 | Barnes et al. |
| 2018/0303473 | A1 | 10/2018 | Spann et al. |
| 2018/0303552 | A1 | 10/2018 | Ryan et al. |
| 2019/0021716 | A1 | 1/2019 | Waugh et al. |
| 2019/0038366 | A1 | 2/2019 | Johnson et al. |
| 2019/0046239 | A1 | 2/2019 | Bobbitt et al. |
| 2019/0069956 | A1 | 3/2019 | Ryan et al. |
| 2019/0090864 | A1 | 3/2019 | Medeiros et al. |
| 2019/0090979 | A1 | 3/2019 | Medeiros et al. |
| 2019/0110785 | A1* | 4/2019 | Serokosz ............ A61B 17/0206 |
| 2019/0216453 | A1 | 7/2019 | Predick et al. |
| 2019/0223854 | A1 | 7/2019 | Baudouin et al. |
| 2020/0054361 | A1 | 2/2020 | Peultier et al. |
| 2020/0085500 | A1 | 3/2020 | Dace et al. |
| 2022/0192645 | A1 | 6/2022 | Peultier et al. |
| 2022/0192647 | A1 | 6/2022 | Josse et al. |
| 2022/0202405 | A1 | 6/2022 | Josse et al. |
| 2022/0202450 | A1 | 6/2022 | Josse et al. |
| 2022/0218417 | A1 | 7/2022 | Josse et al. |

FOREIGN PATENT DOCUMENTS

| | | |
|---|---|---|
| CN | 110381866 | 10/2019 |
| EP | 3331421 A2 | 6/2018 |
| EP | 3351185 | 7/2018 |
| GB | 2528416 A | 1/2016 |
| KR | 10-1446620 | 10/2014 |
| WO | WO 90/02527 | 3/1990 |
| WO | 2007087536 A2 | 8/2007 |
| WO | WO 2018/150214 | 8/2018 |
| WO | WO 2018/150215 | 8/2018 |
| WO | WO 2020/219016 | 10/2020 |
| WO | WO 2020/219018 | 10/2020 |
| WO | WO 2020/219019 | 10/2020 |
| WO | WO 2020/219020 | 10/2020 |

OTHER PUBLICATIONS

International Search Report and Written Opinion for International (PCT) Patent Application No. PCT/US2019/028615, dated Feb. 21, 2020, 8 pages.
International Preliminary Report on Patentability for International (PCT) Patent Application No. PCT/US2019/028615, dated Feb. 21, 2020, 7 pages.
Extended European Search Report for Europe Patent Application No. 19926119.9, dated Nov. 3, 2022, 9 pages.
Official Action for China Patent Application No. 201980095607.3, dated Jan. 25, 2024, 2 pages.
International Search Report and Written Opinion for International (PCT) Patent Application No. PCT/US2019/028624, dated Feb. 21, 2020, 9 pages.
International Preliminary Report on Patentability for International (PCT) Patent Application No. PCT/US2019/028624, dated Sep. 28, 2021, 7 pages.
Extended European Search Report for Europe Patent Application No. 19925802.1, dated Nov. 8, 2022, 10 pages.
Official Action for Europe Patent Application No. 19925802.1, dated Jul. 18, 2024, 3 pages.
International Search Report and Written Opinion for International (PCT) Patent Application No. PCT/US2019/028628, dated Feb. 21, 2020, 7 pages.
International Preliminary Report on Patentability for International (PCT) Patent Application No. PCT/US2019/028628, dated Sep. 28, 2021, 6 pages.
Extended European Search Report for Europe Patent Application No. 19925884.9, dated Nov. 8, 2022, 11 pages.
Official Action for China Patent Application No. 201980095615.8, dated Jan. 23, 2024, 2 pages.
International Preliminary Report on Patentability for International (PCT) Patent Application No. PCT/US2020/027533, dated Oct. 6, 2022, 7 pages.
Extended European Search Report for Europe Patent Application No. 20930065.6, dated Mar. 13, 2024, 5 pages.
Official Action for U.S. Appl. No. 17/605,819, dated Feb. 15, 2024, 10 pages.
Official Action for U.S. Appl. No. 17/605,819, dated Jul. 22, 2024, 12 pages.
Official Action for U.S. Appl. No. 17/605,819, dated Sep. 27, 2024, 13 pages.
Official Action for U.S. Appl. No. 17/606,010, dated Dec. 20, 2023, 16 pages.
Notice of Allowance for U.S. Appl. No. 17/606,010, dated Jul. 9, 2024, 5 pages.
Corrected Notice of Allowance for U.S. Appl. No. 17/606,010, dated Jul. 29, 2024, 2 pages.
Notice of Allowance for U.S. Appl. No. 17/606,010, dated Sep. 16, 2024, 5 pages.
Official Action for U.S. Appl. No. 17/606,011, dated Jan. 18, 2024, 9 pages.
Official Action for U.S. Appl. No. 17/606,011, dated Jul. 3, 2024, 11 pages.
International Search Report for PCT/US2020/027533 date of completion is Jun. 9, 2020 (one page).
International Search Report and Written Opinion for International (PCT) Patent Application No. PCT/US2019/028612, dated Feb. 21, 2020, 7 pages.
International Preliminary Report on Patentability for International (PCT) Patent Application No. PCT/US2019/028612, dated Sep. 28, 2021, 6 pages.
Extended European Search Report for Europe Patent Application No. 19925665.2, dated Nov. 4, 2022, 10 pages.
International Search Report and Written Opinion for International (PCT) Patent Application No. PCT/US2019/028632, dated Feb. 21, 2020, 7 pages.
International Preliminary Report on Patentability for International (PCT) Patent Application No. PCT/US2019/028632, dated Sep. 28, 2021, 6 pages.
Extended European Search Report for Europe Patent Application No. 19925589.4, dated Nov. 7, 2022, 12 pages.
Official Action for China Patent Application No. 201980095623.2, dated Jan. 23, 2024, 2 pages.
Official Action for U.S. Appl. No. 17/606,013, dated Sep. 15, 2023, 5 pages. Restriction Requirement.

(56) References Cited

OTHER PUBLICATIONS

Official Action for U.S. Appl. No. 17/606,013, dated Mar. 21, 2024, 25 pages.
Official Action for U.S. Appl. No. 17/606,013, dated Jun. 12, 2024, 26 pages.
Official Action for China Patent Application No. 202080099220.8, dated Nov. 8, 2024, 10 pages.
Notice of Allowance for U.S. Appl. No. 17/606,011, dated Dec. 5, 2024, 8 pages.
Article 94(3) Communication for Europe Patent Application No. 19925665.2, dated Dec. 17, 2024, 8 pages.
Official Action for U.S. Appl. No. 17/605,779, dated Jan. 21, 2025, 15 pages.
Notice of Allowance for U.S. Appl. No. 17/605,819, dated Jan. 23, 2025, 8 pages.

\* cited by examiner

SURGICAL SYSTEM AND METHOD

CROSS-REFERENCE TO RELATED APPLICATIONS

This application is a National Stage Application of PCT/US2020/027533 filed Apr. 9, 2020, the disclosure of which is hereby incorporated by reference in its entirety.

TECHNICAL FIELD

The present disclosure generally relates to medical devices for the treatment of spinal disorders, and more particularly to a surgical system and a method for correction of a spinal disorder.

BACKGROUND

Spinal disorders such as degenerative disc disease, disc herniation, osteoporosis, spondylolisthesis, stenosis, scoliosis, kyphosis, and other curvature abnormalities, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, ligamentotaxy, corpectomy, discectomy, laminectomy, fusion, fixation and implantable prosthetics. Correction treatments used for positioning and alignment of vertebrae may employ spinal implants including spinal constructs and interbody devices for stabilization of a treated section of a spine. In some cases, the spinal implants may be manipulated with surgical instruments for compression and distraction of vertebrae. This disclosure describes an improvement over these prior technologies.

SUMMARY

In one embodiment, a surgical instrument is provided. The surgical instrument includes a member connectable with a longitudinal element of a surgical distractor connected with vertebrae. At least one blade is connected with the member adjacent to an axis oriented transverse to the longitudinal element and being movable to space tissue adjacent to the vertebrae. The at least one blade being intra-operatively translatable relative to the member along the axis. In some embodiments, surgical systems, constructs, implants and methods are disclosed.

In one embodiment, a surgical system is provided. The surgical system includes a first implant support and a second implant support. The implant supports are engaged with bone fasteners fixed with vertebrae. A surgical distractor having a longitudinal element is engageable with the implant supports. A surgical retractor has a member that is connectable with the longitudinal element. At least one blade is connected with the member adjacent to an axis oriented transverse to the longitudinal element and is movable to space tissue adjacent the vertebrae. The at least one blade is intra-operatively translatable relative to the member along the axis.

In one embodiment, the surgical system includes a first implant support and a second implant support. The implant supports are engaged with bone fasteners fixed with vertebrae. A surgical distractor having a longitudinal element is engageable with the implant supports. A surgical retractor has a member that is connectable with the longitudinal element. At least one blade is connected with the member adjacent to an axis oriented transverse to the longitudinal element. The at least one blade is intra-operatively translatable and rotatable relative to the member about the axis to space tissue adjacent the vertebrae. A locking tool is engageable with the implant supports in a configuration to resist movement of the bone fasteners relative to the vertebrae.

BRIEF DESCRIPTION OF THE DRAWINGS

The present disclosure will become more readily apparent from the specific description accompanied by the following drawings, in which.

DETAILED DESCRIPTION

Figure 1:
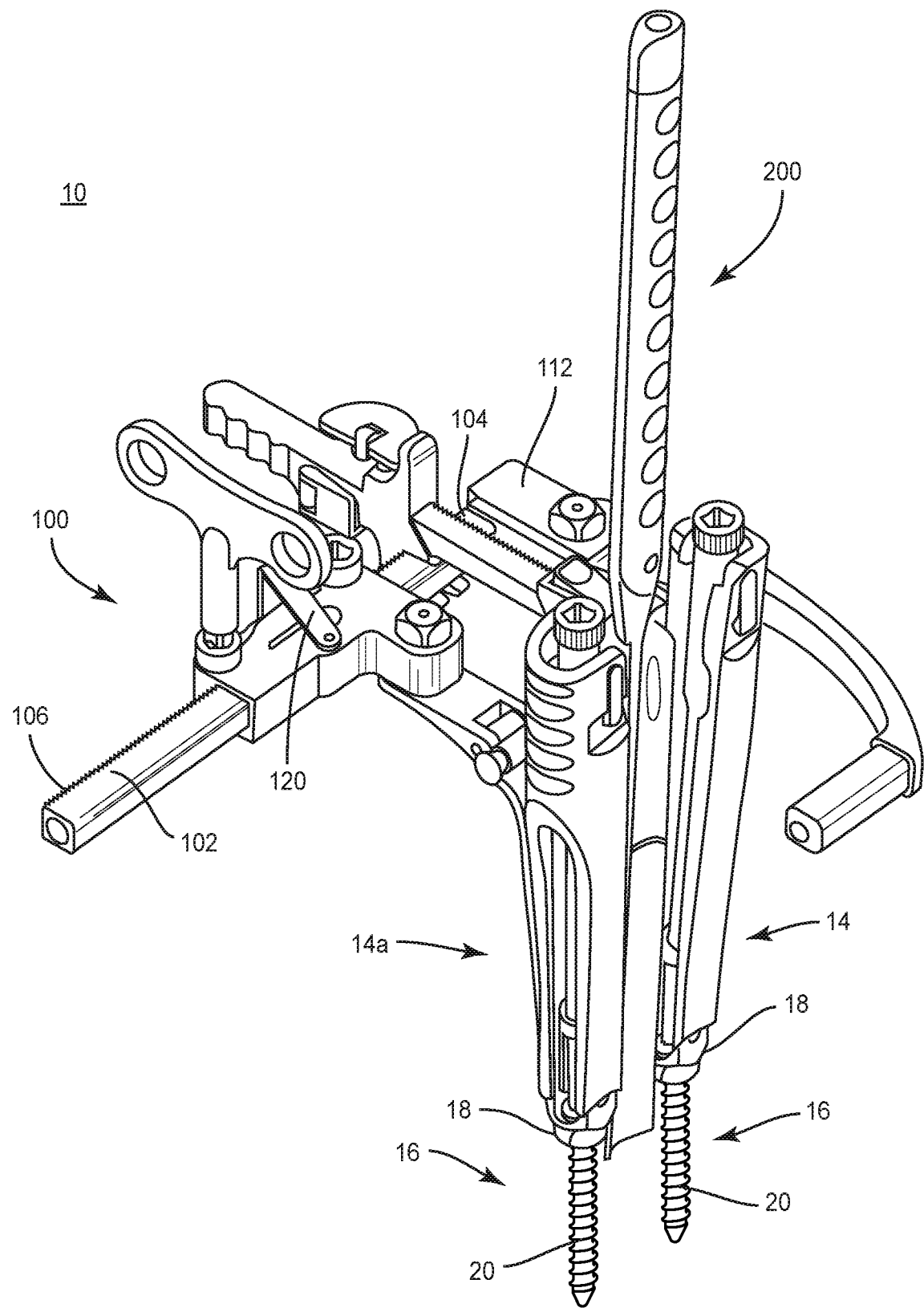
FIG. 1 is a perspective view of components of one embodiment of a surgical system in accordance with the principles of the present disclosure.

The exemplary embodiments of the system and related methods of use disclosed are discussed in terms of medical devices for the treatment of musculoskeletal disorders and more particularly, in terms of a surgical system and method for correction of a spine disorder. In some embodiments, the present surgical system includes surgical instruments and/or spinal implants that can be employed with methods in a configuration, which allows vertebral manipulation to treat spinal disorders, as described herein, for managing lordosis and/or kyphosis restoration. In some embodiments, the present surgical system includes surgical instruments and/or spinal implants that can be employed with methods in a configuration, which allows for parallel distraction and/or compression of vertebral tissue. In some embodiments, the present surgical system and methods include a surgical retractor instrument configured to provide functionality and space vertebral tissue, while reducing crowding of surgical instrumentation in a working space at a surgical site.

In some embodiments, the present surgical system and methods include one or more surgical trauma instruments. In some embodiments, the present surgical system includes one or more surgical instruments and/or spinal implants that are utilized with a method to correct complex spinal deformities. In some embodiments, the present surgical system includes one or more surgical instruments and/or spinal implants that are utilized with a method to treat degenerative spinal disorders and/or employed with transforaminal lumbar interbody fusion procedures. In some embodiments, the present surgical system includes one or more surgical instruments configured for utilization with a sagittal adjusting screw (SAS), a fixed axis screw (FAS) and/or a multi-axial screw (MAS). In some embodiments, the present surgical system comprises one or more surgical instruments including a single distractor to treat degenerative spinal disorders, for example, for disposal along a side of vertebrae oriented for decompression and/or interbody cage insertion.

In some embodiments, the present surgical system comprises one or more surgical instruments including a retractor configured to space tissue adjacent a surgical site. In some embodiments, the present surgical system includes a distractor assembly and the retractor is connected with the distractor assembly. In some embodiments, the components of the present surgical system are employed with a method of treating a spine, which includes the steps of distracting vertebral tissue and intra-operatively manipulating a blade of the retractor. In some embodiments, the step of manipulating includes moving the blade relative to the distractor assembly and/or a body of a patient. In some embodiments, the step of manipulating includes moving the blade to adjust a depth of the blade within the body of the patient and/or a length of the retractor relative to the distractor assembly and/or the body. In some embodiments, the blade has an adjustable length and/or an adjustable retraction angle relative to the distractor assembly and/or the body of the patient. In some embodiments, the blade is extendable and/or expandable relative to the retractor. In some embodiments, the retractor includes a single blade disposed along a selected side of a surgical pathway or opening, for example, a tissue incision that communicates with vertebral tissue. In some embodiments, the single blade spaces vertebral tissue in a configuration to avoid crowding of surgical instrumentation at a surgical site to improve visualization and flexibility in a working space. In some embodiments, the retractor includes a plurality of blades. In some embodiments, the blades may be disposed with a single tissue incision, multiple adjacent tissue incisions, along a selected side of a tissue incision and/or along opposing sides of a tissue incision. In some embodiments, the retractor includes one or more blades, each blade having a uniform length. In some embodiments, the retractor includes one or more blades having the same or different widths along a length. In some embodiments, the retractor includes a telescopic blade such that the blade has a rail that slides within a groove of an arm of the retractor.

In some embodiments, the present surgical system comprises one or more surgical instruments including a retractor having at least one blade that can be intra-operatively translated relative to the retractor, the distractor assembly and/or a body of a patient, to adjust the length of the retractor. In some embodiments, a length of the at least one blade can be expanded relative to the retractor, the distractor assembly and/or a body of a patient, from 60 to 100 millimeters (mm). In some embodiments, the at least one blade can be fixed at a selected length relative to the retractor, the distractor assembly and/or a body of a patient. In some embodiments, the at least one blade is in a ratchet configuration to fix or lock the at least one blade at a selected length. In some embodiments, the ratchet configuration includes an arm of the retractor including a receptacle defining a groove and the at least one blade is frictionally engageable with the groove of the receptacle to selectively fix the at least one blade in a position, for example, a selected length. In some embodiments, the arm and the at least one blade of the retractor are configured in a dovetail connection. In some embodiments, the arm and the at least one blade of the retractor are configured in a key slot configuration. In some embodiments, the receptacle includes a plurality of openings and the at least one blade includes at least one projection disposable with a selected opening of the plurality of openings to lock the at least one blade in a selected position, for example, a selected length. In some embodiments, the at least one projection is biased to a locking orientation. In some embodiments, the blade can be locked at a selected length in increments of 2 mm.

In some embodiments, the at least one blade has an adjustable retraction angle relative to the distractor assembly and/or the body of the patient. In some embodiments, the retraction angle of the at least one blade can include up to 50 degrees of angulation from a pivot point. In some embodiments, the blade can be angled in 5 degree increments. In some embodiments, the retraction angle of the at least one blade is operated and/or released by a button. In some embodiments, the retractor provides 40 mm of retraction. In some embodiments, the blade is released for retraction by pushing a second button.

In some embodiments, the present surgical system includes a distractor assembly and the retractor is connected with the distractor assembly. In some embodiments, the retractor is slidably engaged with a rack of the distractor. In some embodiments, the retractor is configured for soft stabilization with the rack. In some embodiments, distraction or retraction can be performed manually or through a key fixed with the distractor assembly, for example, a turn key. In some embodiments, the key removably engages with the distractor assembly. In some embodiments, the rack of the distractor is closed to limit a clove catch.

In some embodiments, the retractor is employed with a distractor assembly and a locking tool is provided that translates down a screw assembly and locks a receiver of the screw with spring tabs to stabilize the distractor assembly. In some embodiments, the retractor includes a light source that is attached to a portion of the retractor to illuminate the surgical site.

In some embodiments, the present surgical system includes one or more surgical instruments connected with one or more implant supports, for example, connected with bone screws having extender tabs attached thereto. In some embodiments, the one or more surgical instruments are connected with extenders for insertion of an implant, for example, a spinal rod. In some embodiments, the present surgical system includes a compressor/distractor that is utilized for generally parallel compression. In some embodiments, the surgical instrument includes a compressor/distractor having a reversible ratchet with a neutral, freely movable position. In some embodiments, the present surgical system is employed with a procedure for implantation of a bone fastener percutaneously.

In some embodiments, the present surgical system includes a surgical instrument employed with a surgical method including the step of: pre-assembly of the distractor; pre-loading of the alignment guides; preparing for implantation of screws; connecting screw tabs; removal of the alignment guides; attaching a compressor/distractor having an articulating rack for segmental distraction; attaching a retractor for spacing tissue adjacent a surgical site; implanting an interbody and decompressing tissue, inserting a rod length caliper; inserting the rod and setscrews; performing segmental compression; breaking of setscrew tabs; and removing the compressor/distractor and retractor. In some embodiments, the present surgical system is employed with a surgical method including the step of inserting an implant support with a surgical site and connecting a compressor/distractor with the implant support. In some embodiments, the method includes the step of actuating a rack and pinion mechanism disposed with the compressor/distractor to facilitate distraction or compression. In some embodiments, the method includes the step of connecting a retractor to the compressor/distractor and actuating a blade of the retractor to space tissue adjacent the surgical site. In some embodiments, the retractor is provided to maintain the tissue in a medial-lateral orientation creating a channel for accessing the spine anatomy. In some embodiments, the present surgical system is employed with a surgical technique for the implantation of spinal implants, for example, spinal rods and setscrews. In some embodiments, the spinal rods and setscrews are implanted percutaneously. In some embodiments, the spinal rods are reduced relative to a screw head. In some embodiments, the present surgical system is employed with a surgical technique for release of pressure applied during spinal rod reduction.

In some embodiments, the present surgical system includes a surgical instrument configured to compress or distract and restore curvature of a spine. In some embodiments, the present surgical system includes instruments and tools for correcting a sagittal deformity and rebalancing a spine of a body. In some embodiments, the present surgical system is employed to treat degenerative deformities of a spine in a sagittal plane, for example, degenerative kyphosis. In some embodiments, the present surgical system is employed to treat hyper-kyphosis, flat lumbar back, including disorders that create an unbalance of a body and loss of alignment between body parts. In some embodiments, the present surgical system provides a selected amount of correction to apply a selected balance to a spine and provides control and adjustment to the amount of correction. In some embodiments, the present surgical system includes a series of tools and instruments that allow formulation of a type of correction applied and can control the correction stabilization using posterior instrumentation.

In some embodiments, one or all of the components of the surgical system are disposable, peel-pack, pre-packed sterile devices used with a spinal construct. One or all of the components of the surgical system may be reusable. The surgical system may be configured as a kit with multiple sized and configured components.

In some embodiments, the present disclosure may be employed to treat spinal disorders, for example, degenerative disc disease, disc herniation, osteoporosis, spondylolisthesis, stenosis, scoliosis, kyphosis and other curvature abnormalities, tumor and fractures. In some embodiments, the present disclosure may be employed with other osteal and bone-related applications, including those associated with diagnostics and therapeutics. In some embodiments, the disclosed surgical system and methods may be alternatively employed in a surgical treatment with a patient in a prone or supine position, and/or employ various surgical approaches to the spine, including posterior and/or posterior mid-line and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternative embodiments are disclosed. Reference is made to the exemplary embodiments of the present disclosure, which are illustrated in the accompanying figures. Turning to FIGS. 1-9, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, for example, composites of metals and calcium-based ceramics, composites of PEEK and calcium based ceramics, composites of PEEK with resorbable polymers, totally resorbable materials, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of surgical system 10 are configured for engagement with spinal constructs attached with vertebrae to manipulate tissue and/or correct a spinal disorder, for example, a sagittal deformity, as described herein. In some embodiments, surgical system 10 may be employed with a surgical procedure, for example, corpectomy, discectomy and/or fracture/trauma treatment and may include fusion and/or fixation that employ implants to restore the mechanical support function of vertebrae.

Surgical system 10 includes a surgical instrument, for example, an implant support 14 and an implant support 14a, similar to implant support 14 as described herein. Implant supports 14, 14a are connectable with a spinal implant, for example, a bone fastener 16. Bone fastener 16 includes a receiver 18 and a screw shaft 20, as shown in FIG. 1. Screw shaft 20 is fixed with patient tissue in use of fastener 16. Each receiver 18 is connectable with one of implant supports 14, 14a to releasably engage a surgical instrument, for example, a compressor/distractor 100 to distract and/or compress tissue. Each receiver 18 is configured for disposal of a component of a spinal construct, for example, a spinal rod (not shown). Each receiver 18 includes an inner surface having a thread form. Bone fastener 16 includes screw shaft 20 configured to penetrate tissue, for example, bone.

Figure 2:
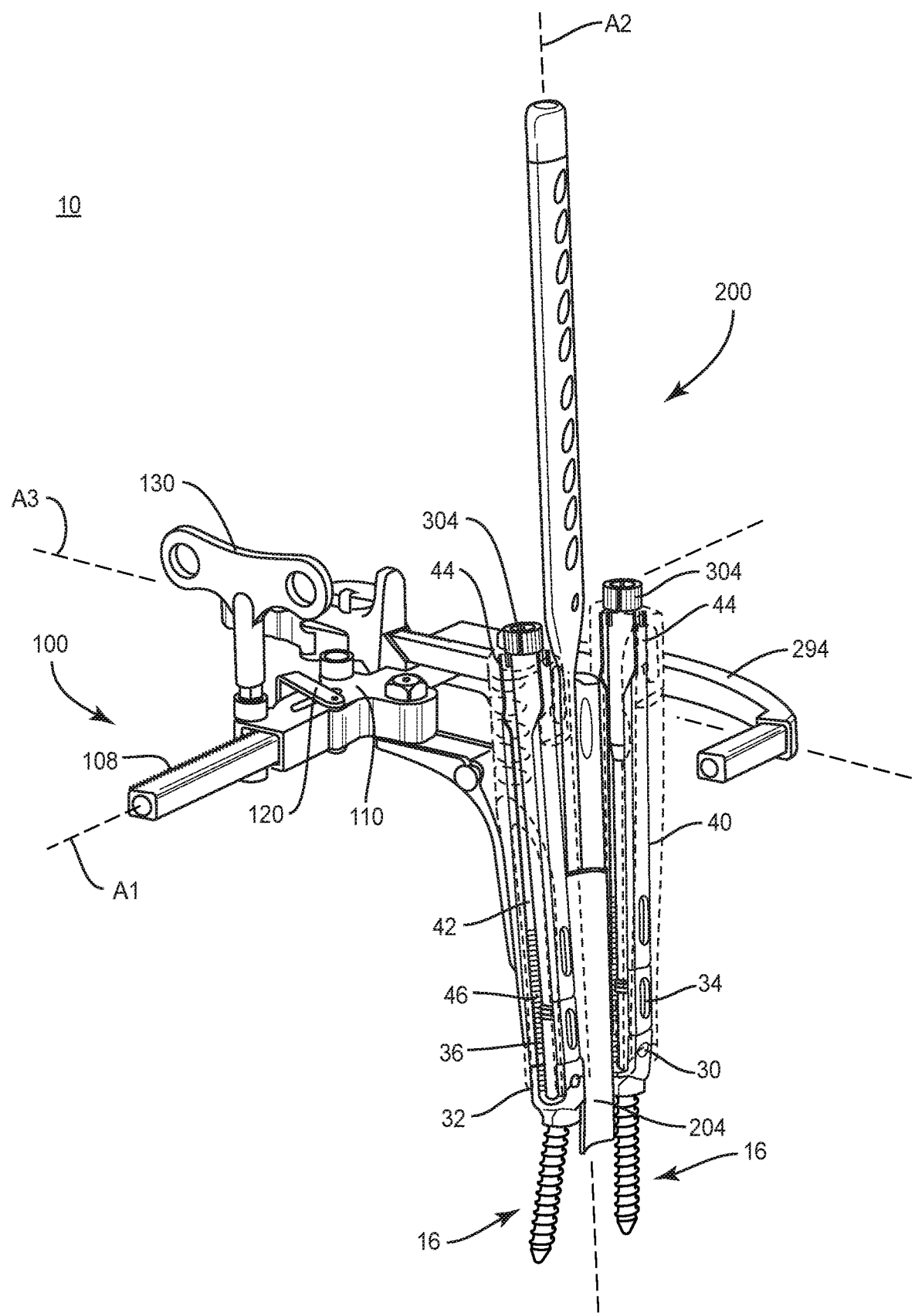
FIG. 2 is a perspective view, in part phantom, of components of one embodiment of a surgical system in accordance with the principles of the present disclosure.

An arm 30 includes or is connected to a break-away tab 34 that is frangibly connected to arm 30, as shown in FIG. 2, such that manipulation of tab 34 relative to arm 30 can fracture and separate tab 34 from arm 30 at a predetermined force and/or torque limit. An arm 32 similarly includes or is connected to a break-away tab 36 that is frangibly connected to arm 32 such that manipulation of tab 36 relative to arm 32 can fracture and separate tab 36 from arm 32 at a predetermined force and/or torque limit. In some embodiments, as force and/or torque is applied to tabs 34, 36 and resistance increases, for example, the predetermined torque and force limit is approached allowing tabs 34, 36 to break off from arms 30, 32.

In some embodiments, each implant support 14, 14a includes extender tabs 40, 42 that are connectable with tabs 34, 36 and/or bone fastener 16. Each extender tab 40, 42 extends between a proximal end 44 and a distal end 46. Distal ends 46 are configured for slidable disposal of a portion of bone fastener 16, for example, tabs 34, 36. In some embodiments, tabs 34, 36 are configured to releasably fix extender tabs 40, 42 to bone fastener 16 for connecting extender tabs 40, 42 to implant support 14, as described herein.

Compressor/distractor 100 includes a longitudinal element, for example, a rack 102, as shown in FIG. 1. Rack 102 extends between an end 104 and an end 106 defining a longitudinal axis A1. Rack 102 is configured to connect adjacent implant supports 14, 14a to each other and is configured to connect with a retractor 200, as shown in FIG. 1. Rack 102 includes an outer surface having a plurality of teeth, for example, splines 108 engageable with an arm 110, as described herein. Rack 102 includes an arm 112 extending from end 104. Arm 110 is axially translatable along axis A1 relative to arm 112. In some embodiments, arm 112 is attached with rack 102, for example, with clips, hooks, adhesives and/or flanges.

Splines 108 and arm 110 are engageable in a bi-directional configuration to facilitate translation of implant supports 14, 14a for distraction and/or compression of tissue. Arm 110 includes a latch 120, which is engageable selectively with splines 108. In various embodiments, latch 120 includes a pinion or pawl (not shown in detail) engageable with splines 108. In some embodiments, latch 120 includes a ratchet configuration and is movable to allow movement in one direction only. In some embodiments, latch 120 includes a clove catch configuration.

Latch 120 is pivotable relative to arm 110 for disposal selectively in one or multiple positions. In various embodiments, the positions include a distraction position, a neutral position, and a compression position. In the distraction position, latch 120 engages rack 102 to allow axial and/or incremental translation of arm 110 relative to arm 112/rack 102. As such, distraction of vertebral tissue connected with implant supports 14, 14a can be performed. Latch 120 is pivotable relative to arm 110 for disposal in a neutral position. In the neutral position, latch 120 disengages from rack 102 to allow free axial translation of arm 110 relative to arm 112/rack 102.

Latch 120 is pivotable relative to arm 110 for disposal in a compression position. In the compression position, latch 120 engages rack 102 to allow axial and/or incremental translation of arm 110 relative to arm 112/rack 102. As such, compression of vertebral tissue connected with implant supports 14, 14a can be performed. A rotatable key 130 includes a gear surface engageable with splines 108 to axially and/or incrementally translate rack 102 to facilitate distraction and/or compression, as described herein.

In some embodiments, connection of implant supports 14, 14a to facilitate correction of a vertebral angle of vertebrae, for example, to achieve a selected lordosis and/or kyphosis, via manipulation of implant supports 14, 14a, as described herein, is provided. In some embodiments, implant supports 14, 14a are connected with compressor/distractor 100 to maintain a corrected vertebral angle of vertebrae during distraction and/or compression, as described herein.

Figure 3:
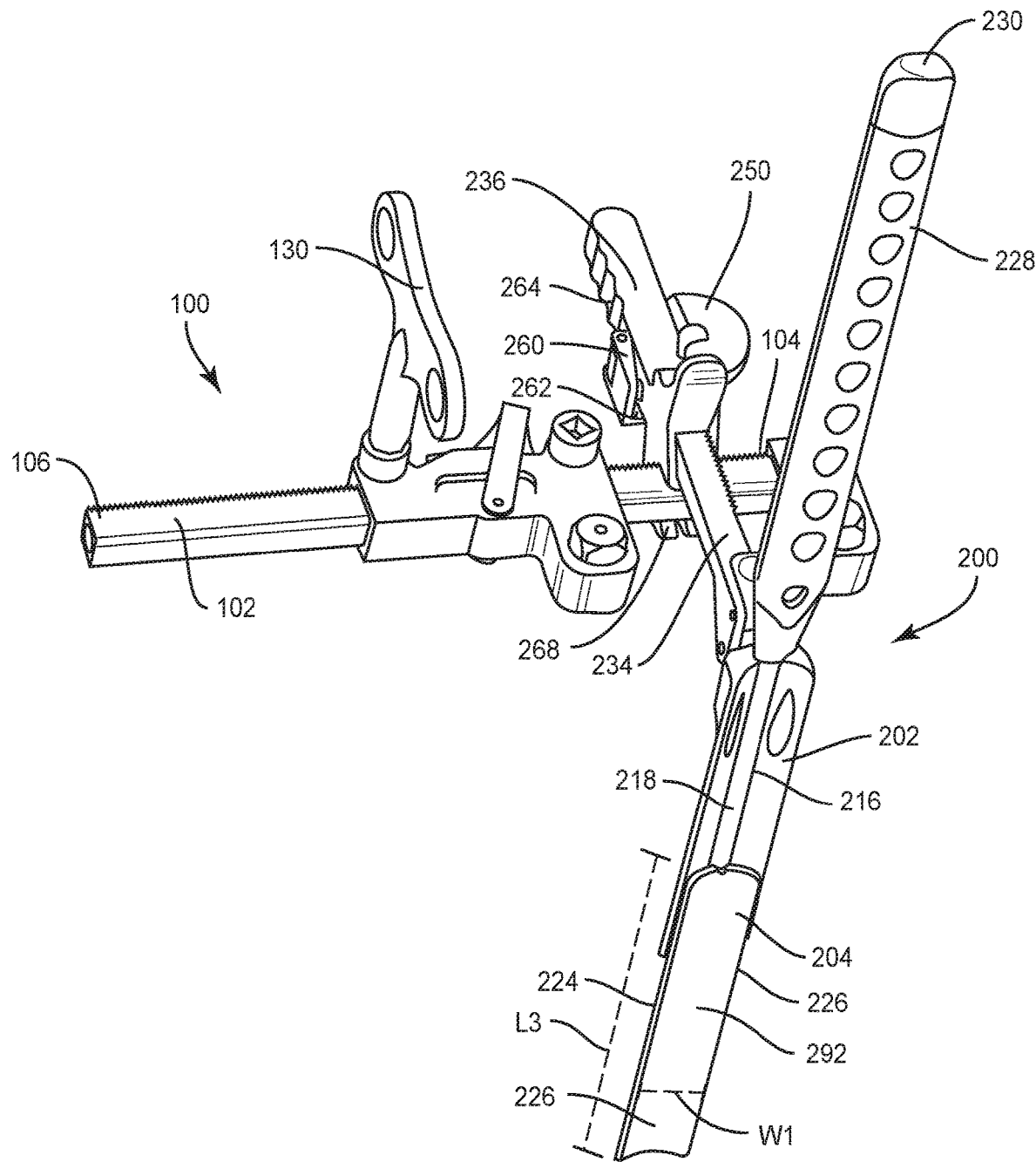
FIG. 3 is a perspective view of components of one embodiment of a surgical system in accordance with the principles of the present disclosure.

Retractor 200 is configured to connect with rack 102 of compressor/distractor 100 to space tissue adjacent vertebrae. Retractor 200 includes a member, for example, arm 202 and a blade 204, as shown in FIG. 3. Blade 204 is connected with arm 202 and is disposed adjacent to an axis A2 oriented transverse relative to axis A1 of rack 102 and is movable to space the tissue adjacent vertebrae. Blade 104 is intra-operatively translatable relative to arm 202 along axis A2 and is intra-operatively rotatable relative to axis A2 to space the tissue. In some embodiments, retractor 200 can include more than one blade 204. In some embodiments, arm 202 and blade 204 are configured in a dovetail connection. In some embodiments, arm 202 and blade 204 are configured in a key slot configuration.

Figure 4:
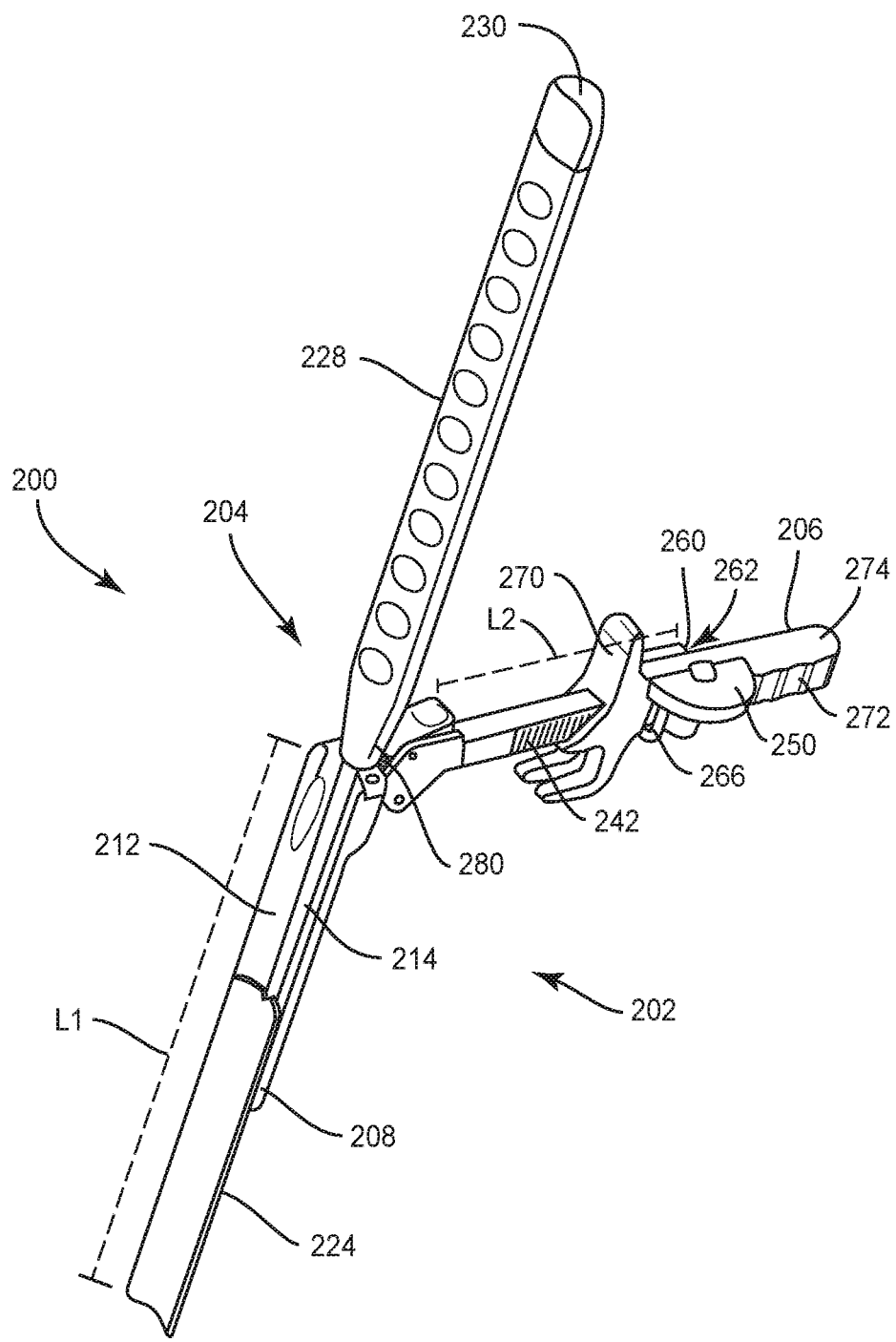
FIG. 4 is a perspective view of components of one embodiment of a surgical system in accordance with the principles of the present disclosure.
Figure 5:
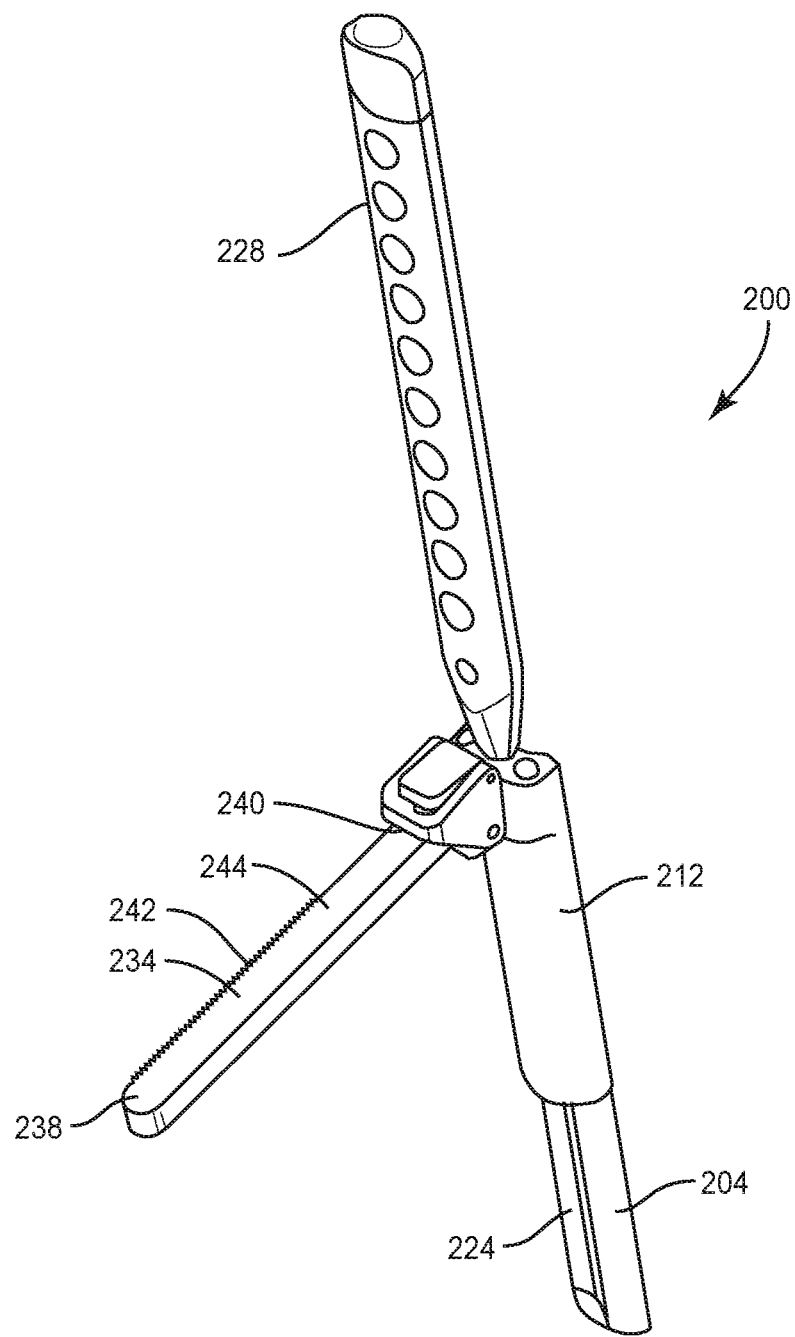
FIG. 5 is a perspective view of components of one embodiment of a surgical system in accordance with the principles of the present disclosure.

Arm 202 includes a proximal end 206 and a distal end 208, as shown in FIG. 4. End 206 is configured for engagement with rack 102, as described herein and end 208 is configured for connection with blade 204. In some embodiments, arm 202 and blade 204 form a ratchet configuration to fix or lock blade 204 at a selected length. In some embodiments, a latch (not shown) is provided to fix or lock blade 204 at a selected length relative to arm 202, compressor/distractor 100 and/or the patient's body. In some embodiments, a locking element provides a rigid fixation of blade 204 relative to arm 202 to fix or lock blade 204 at a selected length relative to arm 202, compressor/distractor 100 and/or the patient's body.

Figure 8:
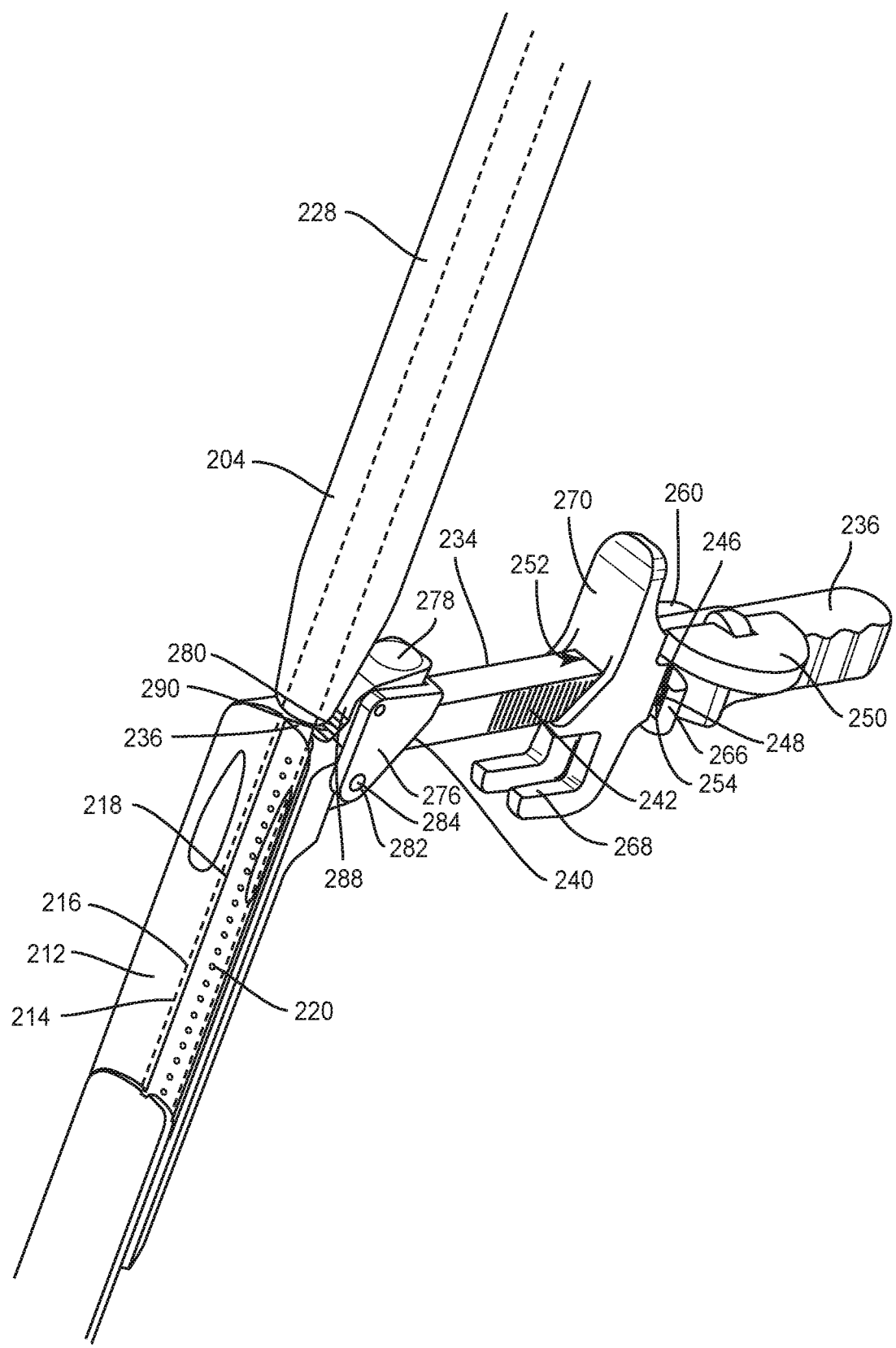
FIG. 8 is a break away view, in part phantom, of the components shown in FIG. 4.

End 208 includes a receptacle 212 configured for disposal of a rail 214 of blade 204. In some embodiments, blade 204 via rail 214 is releasably fixed through a friction engagement with receptacle 212 to selectively fix blade 204 in a position relative to arm 202, compressor/distractor 100 and/or the patient's body. In some embodiments, blade 204 via rail 214 forms a slidable lock with receptacle 212 to selectively fix blade 204 in a position relative to arm 202, compressor/distractor 100 and/or the patient's body. Receptacle 212 includes a wall 216 that defines a longitudinal groove, for example, slot 218 configured for movable disposal of rail 214, as shown in FIG. 8. Slot 218 extends an entire length of receptacle 212. In some embodiments, slot 218 extends only a portion of receptacle 212.

In some embodiments, slot 218 includes a uniform, even surface configuration. In some embodiments, slot 218 may have various surface configurations, for example, rough, arcuate, undulating, porous, semi-porous, dimpled, polished and/or textured. In some embodiments, slot 218 may be disposed at alternate orientations, relative to axis A2, for example, transverse, perpendicular and/or other angular orientations for example, acute or obtuse, coaxial and/or may be offset or staggered.

Figure 6:
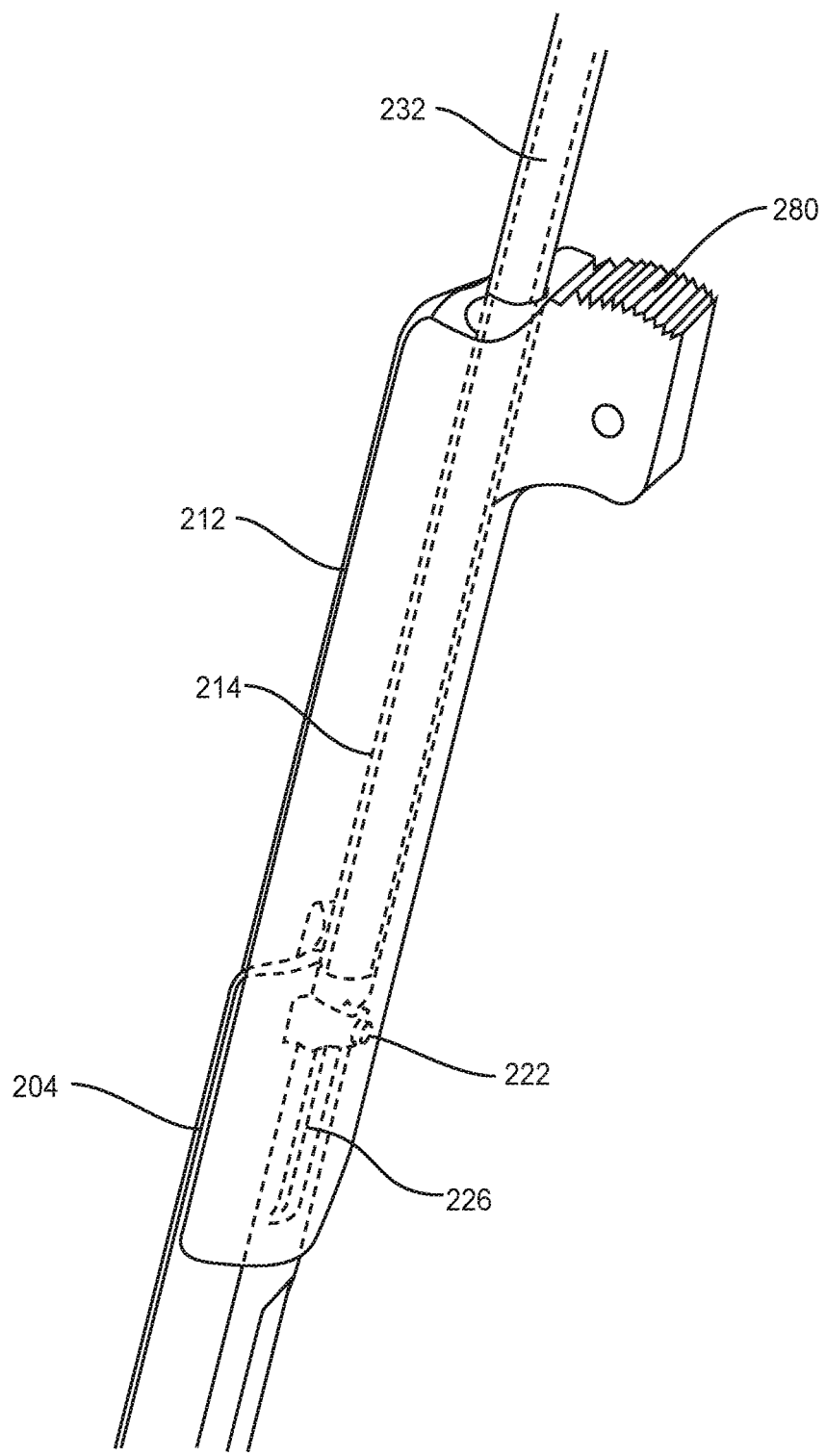
FIG. 6 is a break away view, in part phantom, of the components shown in FIG. 4.
Figure 7:
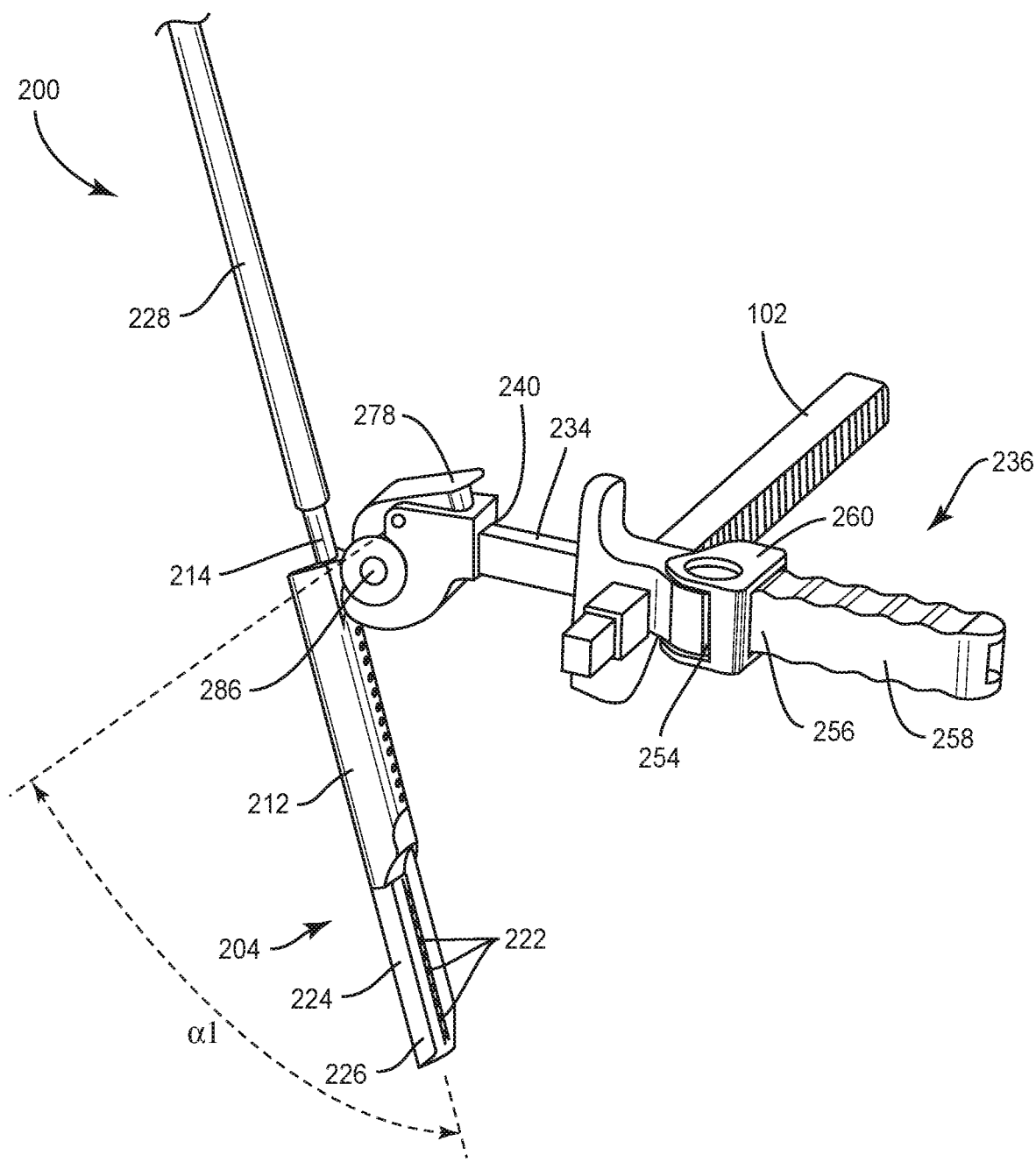
FIG. 7 is a perspective view of components of one embodiment of a surgical system in accordance with the principles of the present disclosure.

Wall 216 defines a plurality of openings 220, as shown in FIG. 8, which are disposed along the length of slot 218. An outer surface 224 of a distal end 226 of blade 204 defines a projection 222, as shown in FIGS. 6 and 7. Projection 222 is configured for disposal with a selected opening 220 to lock blade 204 into a selected position. Projection 222 is biased to a locking orientation when disposed within a selected opening 220. In some embodiments, blade 204 includes a plurality of projections 222, as shown in FIG. 7. In some embodiments, openings 220 and the corresponding projection 222 are round. In some embodiments, openings 220 and projection 222 may be variously configured and dimensioned, for example, oval, oblong, square, rectangular, polygonal, irregular, uniform, non-uniform, offset, staggered, tapered, consistent and/or variable. In some embodiments, openings 220 may be variously configured and dimensioned, for example, indents, recesses and/or detents.

A handle 228 is configured to selectively adjust blade 204 at selected length L1 relative to compressor/distractor 100 and/or the patient's body through engagement with rail 214, as shown in FIG. 4. Handle 228 includes a button 230 connected to an end of a plurality of internal rods 232 that are telescopically disposed within handle 228 and rail 214, as shown in FIGS. 4 and 6. Button 230 is depressed and then rotated in a direction shown by arrow C in FIG. 11 and rods 232 are translated in a direction shown by arrows D in FIG. 12 to adjust the length L1 of blade 204. In some embodiments, blade 204 is locked at selected length L1 in increments of 2 mm. In some embodiments, length L1 can be from 60 to 100 mm relative to retractor 200, compressor/distractor 100 and/or a body of a patient.

End 206 of arm 202 includes a support 234 connected with blade 204 and a sleeve 236 connected with rack 102, as shown in FIGS. 7 and 8. Support 234 is translatable relative to sleeve 236 in a bi-directional configuration such that support 234 has a variable length L2 relative to rack 102 to facilitate retraction within the surgical site. In some embodiments, length L2 can be up to 40 mm. In some embodiments, length L2 can be from 10 to 60 mm.

Support 234 includes a proximal end 238 and a distal end 240 defining a longitudinal axis A3. Axis A3 is transverse relative to axes A1 and A2. Support 234 includes a plurality of teeth, for example, splines 242 defined from a surface 244 of support 234 configured for engagement with a key 250 of sleeve 236 including a shaft 248 having threads 246. Splines 242 and threads 246 of key 250 are engageable to translate support 234 relative to sleeve 236. End 238 of support 234 is disposed within an opening 252 of sleeve 236 and threads 246 of key 250 engage with splines 242 through an opening 254 defined from a surface 256 of a side 258 of sleeve 236, as shown in FIGS. 7 and 8.

A one-way latch 260 is configured to engage threads 246 of key 250 to lock sleeve 236 into a fixed position relative to support 234, as shown in FIG. 4. Latch 260 includes a biasing member, for example, spring 262 disposed between a side 264 of sleeve 236 and a flange 266. Flange 266 is configured for engagement with threads 246 of key 250 to tension, and thereby lock key 250 in place such that sleeve 236 is locked in a fixed position relative to support 234. Translation of support 234 is initiated when latch 260 is in a non-locking orientation and flange 266 disengages with threads 246 of key 250. In some embodiments, support 234 can be manually translated relative to sleeve 236.

Sleeve 236 includes a ledge 268 at a proximal end 270 configured for engagement with rack 102, as shown in FIGS. 3 and 8. In some embodiments, rack 102 is slidably engaged with ledge 268. In some embodiments, ledge 268 may have various surface configurations, for example, rough, arcuate, undulating, porous, semi-porous, dimpled, polished and/or textured.

Sleeve 236 includes a gripping portion 272 at a distal end 274, as shown in FIG. 4. In some embodiments, gripping portion 272 may have various surface configurations, for example, rough, arcuate, undulating, porous, semi-porous, dimpled, polished and/or textured.

End 240 of support 234 includes a pivot housing 276 and a lock, for example, button 278, as shown in FIGS. 7 and 8. Housing 276 is configured for rotatable engagement with receptacle 212 such that blade 204 is selectively rotatable to a fixed position relative to compressor/distractor 100. Receptacle 212 includes a splined tongue 280 defining an opening 282 configured for engagement with housing 276. A pivot point is created through engagement of opening 282, an opening 284 of housing 276 and a pin 286 disposed within openings 282 and 284. To rotate blade 204 into a position, for example, a selected retraction angle $\alpha 1$, as shown in FIG. 7, handle 228 is manually rotated by a user. In some embodiments, angle $\alpha 1$ includes up to 50 degrees of angulation from the pivot point. In some embodiments, blade 204 is angled in 5 degree increments. In some embodiments, angle $\alpha 1$ includes an angle in a range of 0 to 90 degrees from the pivot point.

The retraction angle of blade 204 is fixed or released by button 278. As shown in FIG. 8, when button 278 is depressed and biased in a locking orientation, a tooth 288 of button 278 will fixedly engage with a plurality of teeth, for example, splines 290 of tongue 280 to lock blade 204 at a selected retraction angle. In some embodiments, button 278 includes a biasing member, for example, a spring (not shown) to facilitate biasing button 278 in the locking orientation. Button 278 is in a non-locking orientation when button 278 is lifted, causing tooth 288 to disengage from splines 290.

End 226 of blade 204 is configured for engagement with tissue of a surgical site. End 226 includes an inner surface 292 and outer surface 224 for engagement with tissue, as shown in FIG. 3. End 226 includes a width W1. In some embodiments, width W1 is from about 2 to about 20 mm. In some embodiments, the width is uniform or non-uniform. In some embodiments, end 226 is tapered. End 226 includes a length L3. In some embodiments, length L3 is from about 4 to about 100 mm. In some embodiments, all or only a portion of blade 204 may have various cross-section configurations, for example, arcuate, cylindrical, oblong, rectangular, polygonal, undulating, irregular, uniform, non-uniform, consistent, variable, and/or U-shape. Blade 204 is movable within multiple orientations relative to compressor/distractor 100 and/or the body of the patient to selectively space tissue.

Figure 9:
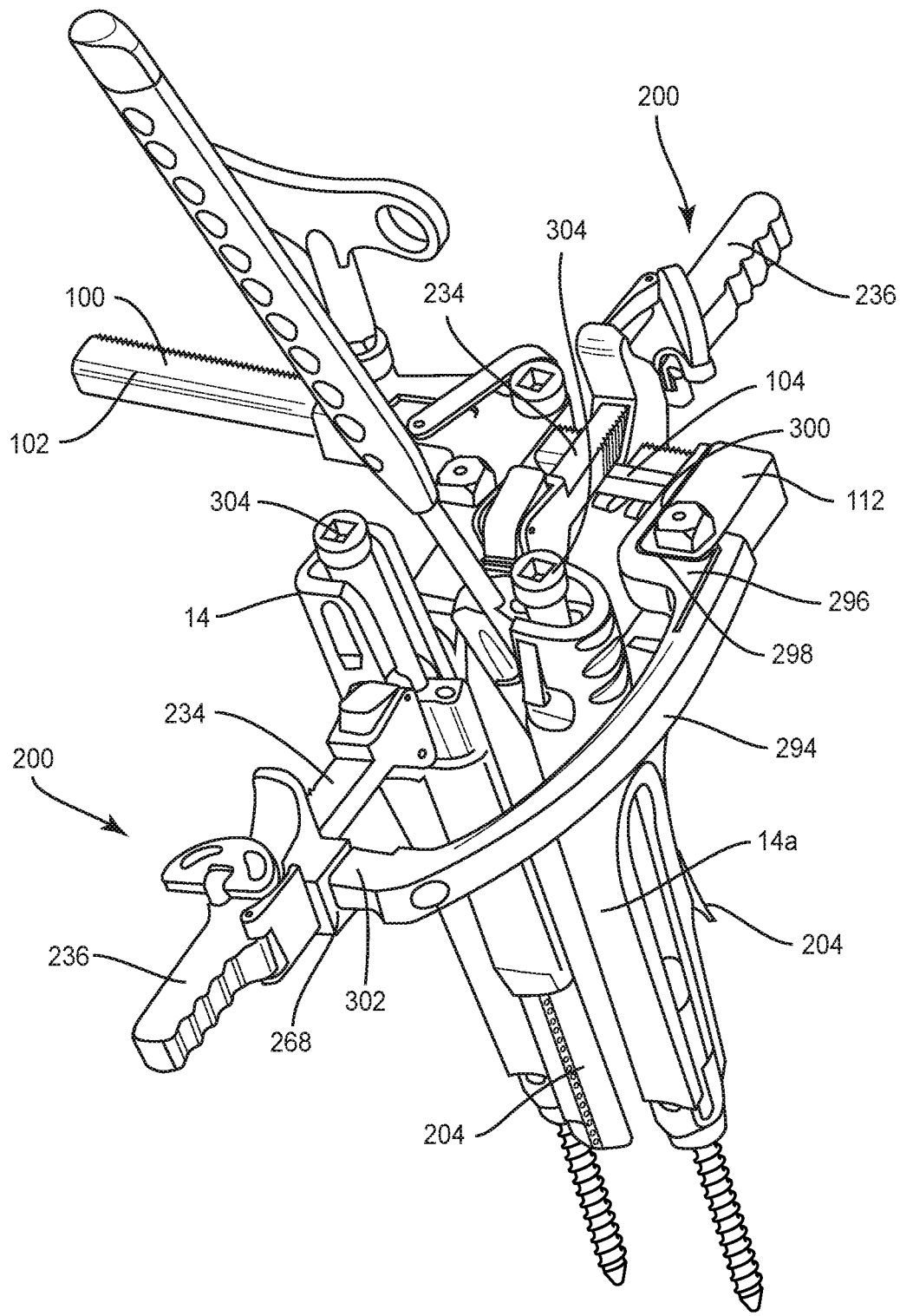
FIG. 9 is a perspective view of components of one embodiment of a surgical system in accordance with the principles of the present disclosure.

As shown in FIGS. 1-8, retractor 200 includes only one blade 204. In some embodiments, as shown in FIG. 9, retractor 200 can include one or more blades 204, for example, two blades 204 and/or surgical system 10 can include two sleeve 236/support 234 assemblies. An arm 294 is configured to connect with compressor/distractor 100 such that a second retractor 200 having a second blade 204 can be employed. Arm 294 includes a proximal end 296 configured for engagement with arm 112 of rack 102 of compressor/distractor 100. End 296 includes an indented portion 298 configured for engagement with arm 112 and a flange 300 configured for engagement with end 104 of rack 102. A distal end 302 of arm 294 is configured for engagement with ledge 268 of sleeve 236 of second retractor 200 to lock retractor 200 with arm 294.

In some embodiments, each blade 204 can have a uniform length. In some embodiments, each blade 204 can have the same or different widths W1 along a length. It is to be understood that the manner by which dimensions or directions are indicated does not limit scope of the invention, such as limiting the orientation that any component may be disposed, connected, or moved. In some embodiments, a light source (not shown) is disposed with retractor 200 to provide illumination to the surgical site.

Figure 11:
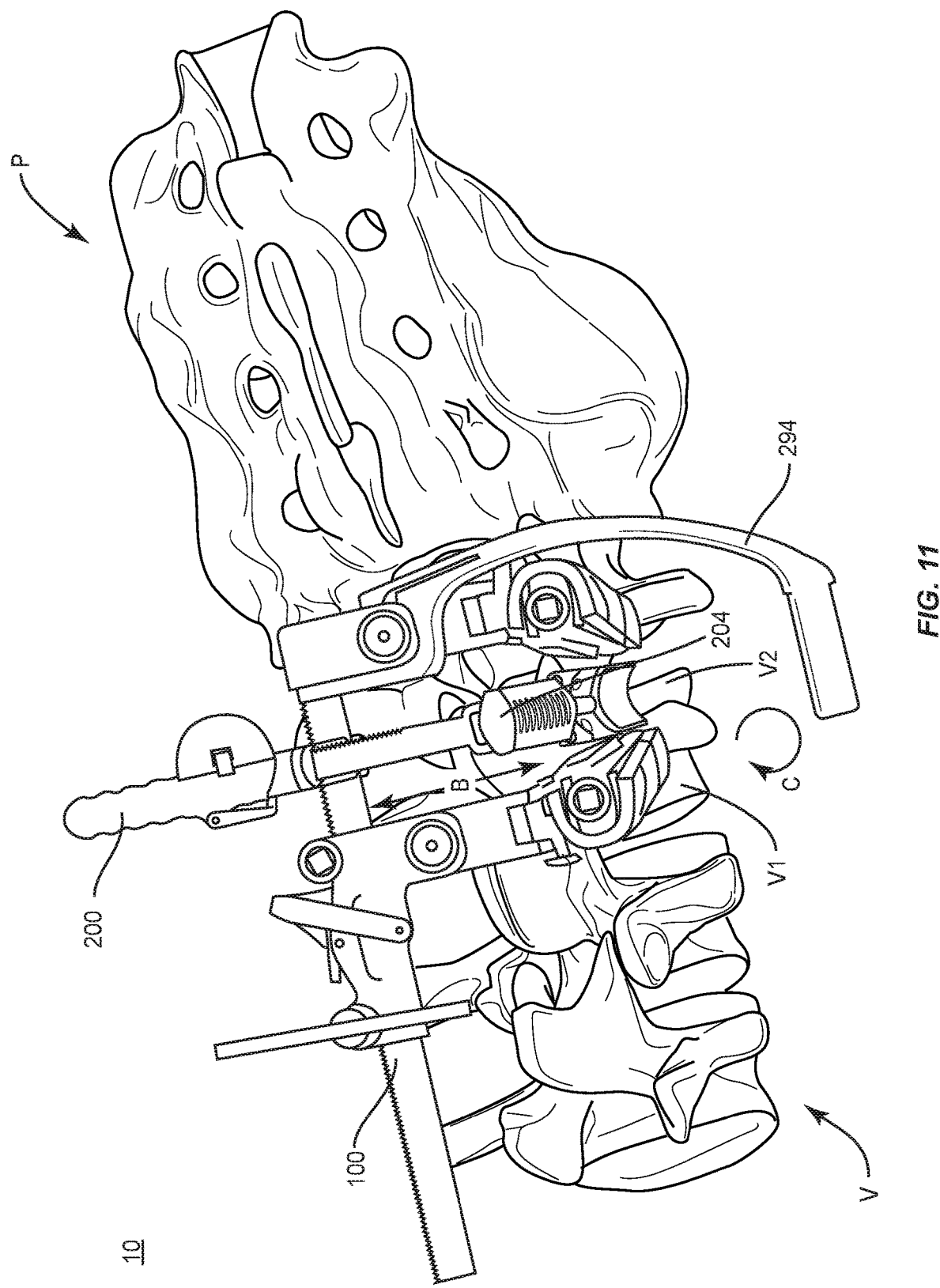
FIG. 11 is a perspective view of components of one embodiment of a surgical system in accordance with the principles of the present disclosure disposed with vertebrae.
Figure 12:
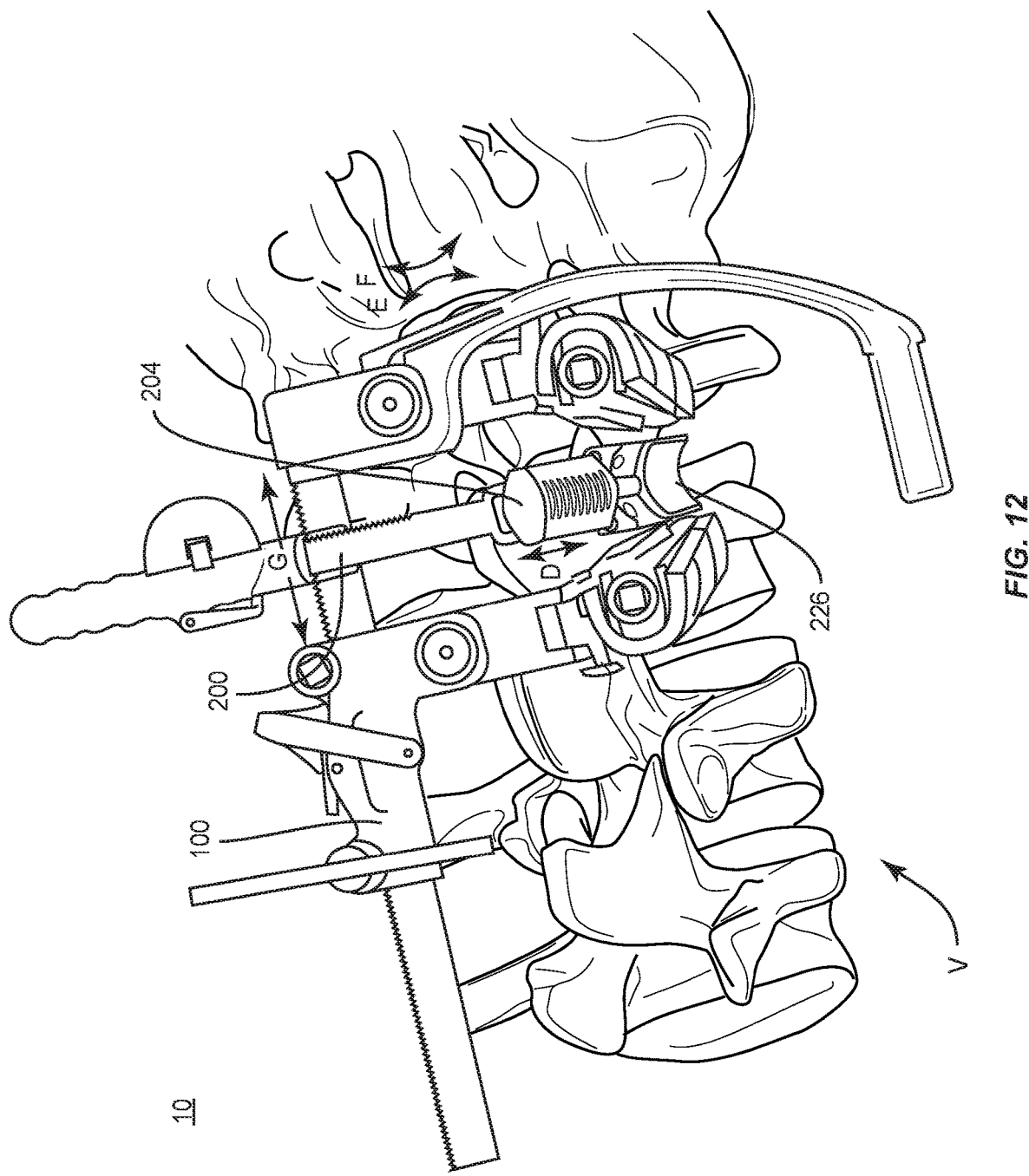
FIG. 12 is a break away view of the components and vertebrae shown in FIG. 11.

In assembly, operation and use, surgical system 10, similar to the systems and methods described herein, is employed with a surgical procedure, for treatment of a spine of a patient including vertebrae V, as shown in FIGS. 11 and 12. Surgical system 10 may also be employed with surgical procedures, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Surgical system 10 is employed with a procedure for treatment of an applicable condition or injury of an affected section of a spinal column and adjacent areas within a body. In some embodiments, components of surgical system 10 are configured for insertion with a vertebral space to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, surgical system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area.

An incision is made in the body of a patient P and a cutting instrument (not shown) creates a surgical pathway for implantation of components of surgical system 10. A preparation instrument (not shown) can be employed to prepare tissue surfaces of vertebrae V, as well as for aspiration and irrigation of a surgical region. Pilot holes or the like are made in selected vertebrae V1 and V2 for receiving bone fasteners 16. Bone fasteners 16 are engaged with vertebrae V for example, along a lateral side and extenders 40, 42 are engaged with bone fasteners 16.

Implant supports 14, 14a are connected with extenders 40, 42, as described herein. A driver (not shown) is disposed adjacent vertebrae V at a surgical site and is manipulated to drive, torque, insert or otherwise connect bone fasteners 16 with vertebrae for example, V1 and V2, as shown in FIG. 11.

Compressor/distractor 100 is connected with implant supports 14, 14a to allow for distraction and/or compression of vertebrae V connected with extenders 40, 42. Retractor 200 is connected with rack 102 of compressor/distractor 100 via ledge 268. Support 234 is connected to sleeve 236 and movable engagement between splines 242 and key 250 via key 250 rotation translates support 234 along axis A3, in a direction shown by arrows B in FIG. 11, to position blade 204 within the surgical pathway. Latch 260 is depressed and flange 266 of latch 260 engages with threads 246 of key 250 to lock sleeve 236 into a fixed position relative to support 234.

Button 230 of handle 228 is depressed and rotated, in a direction shown by arrow C in FIG. 11, and rail 214 is translated along axis A2 within slot 218, in a direction shown by arrows D in FIG. 12, to selectively adjust the length of blade 204 relative to compressor/distractor 100 and/or the body of the patient for contacting tissue. As rail 214 translates within slot 218, projection 222 is disposed within a selected opening 220 of receptacle 212 to lock blade 204 into a selected length relative to compressor/distractor 100 and/or the body of the patient to selectively space tissue. Handle 228 is rotated, in a direction shown by arrows E or F in FIG. 12, to adjust the retraction angle of blade 204 relative to compressor/distractor 100 and/or the body of the patient to separate the tissue. In some embodiments, button 278 is depressed and tooth 288 engages with splines 290 to place blade 204 in a locked orientation at a selected retraction angle relative to compressor/distractor 100 and/or the body of the patient to maintain separation of the tissue. In some embodiments, button 278 is lifted causing tooth 288 to disengage from splines 290 to place blade 204 in a non-locking orientation to release blade 204 from the selected retraction angle.

Figure 10:
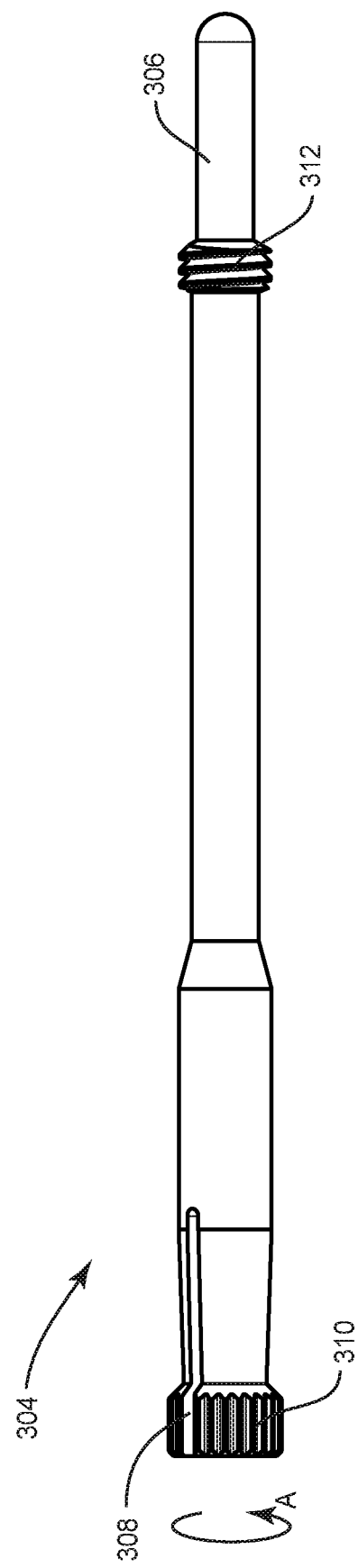
FIG. 10 is a side view of components of one embodiment of a surgical system in accordance with the principles of the present disclosure.

In some embodiments, a locking tool 304, as shown in FIGS. 2, 9 and 10, is engageable with implant supports 14, 14a in a configuration to resist movement of bone fasteners 16 relative to vertebrae. Tool 304 is translated through implant support 14 and a distal end 306 of tool 304 engages with receiver 18, including the inner surface having the thread form. Tool 304 is rotated at a knob 308 located at a proximal end 310, in a direction shown by arrow A in FIG. 10, and a threaded portion 312 at end 306 is threadingly engaged with the thread form of receiver 18 to stabilize bone fastener 16 engaged with vertebrae V1 during compression/distraction as described herein, manipulation of vertebrae and/or manipulation of components of surgical system 10. A second tool 304 is translated through implant support 14a and end 306 of tool 304 engages with receiver 18. Tool 304 is rotated at knob 308, in the direction shown by arrow A, and threaded portion 312 is threadingly engaged with the thread form of receiver 18 to stabilize bone fastener 16 engaged with vertebrae V2.

Latch 120 is pivotable relative to arm 110 for disposal in a distraction position. In the distraction position, latch 120 engages rack 102 to allow axial and/or incremental translation of arm 110 relative to arm 112/rack 102, in the direction shown by arrows G in FIG. 12, to distract vertebral tissue connected with implant supports 14, 14a. The applied distraction forces on bone fasteners 16 will allow for opening of the foramen and the posterior wall of the spinal disc. Latch 120 can be released or re-adjusted at any time during the procedure. Latch 120 is pivotable relative to arm 110 for disposal in a neutral position (not shown). In the neutral position, latch 120 allows free axial translation of arm 110 relative to arm 112/rack 102.

In some embodiments, a measuring device, for example, a caliper (not shown) is utilized to determine a length of spinal rod (not shown). The caliper is engaged with implant supports 14, 14a such that a distance between bone fasteners 16 can be determined. Determining the distance provides a length of the rod for connection with bone fasteners 16.

In some embodiments, a rod inserter (not shown) is engaged with a spinal rod. The rod inserter directs and/or guides the spinal rod into receiver 18. In some embodiments, a percutaneous endoscopic lumbar discectomy is utilized.

In some embodiments, a driver (not shown) is utilized to engage a set screw (not shown) with bone fasteners 16. The driver directs and/or guides the set screw through each of implant supports 14, 14a into engagement with receivers 18. The set screw engages receivers 18 to fix the spinal rod. In some embodiments, if segmental compression is required, the set screws are loosened and latch 120 is pivotable relative to arm 110 for disposal in a compression position. In the compression position, latch 120 engages rack 102 to allow axial and/or incremental translation of arm 110 relative to arm 112/rack 102, to compress vertebral tissue connected with implant supports 14, 14a. In some embodiments, rotatable key 130 includes a gear surface engageable with splines 108 to axially and/or incrementally translate rack 102 to facilitate distraction and/or compression, as described herein.

Upon completion of a procedure, as described herein, the surgical instruments, assemblies and non-implanted components of surgical system 10 are removed and the incision(s) are closed. One or more of the components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10. In some embodiments, surgical system 10 may include one or a plurality of plates, connectors and/or bone fasteners for use with a single vertebral level or a plurality of vertebral levels. In some embodiments, one or more spinal implants of surgical system 10, may be engaged with tissue in various orientations, for example, series, parallel, offset, staggered and/or alternate vertebral levels. In some embodiments, the spinal implant of surgical system 10 may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, surgical system 10 includes one or a plurality of alternative surgical instruments, each configured for mating engagement in a quick release configuration with spinal constructs, as described herein. This configuration facilitates the interchangeability of the spinal constructs with the alternative surgical instruments. In some embodiments, surgical system 10 includes one or a plurality of alternative surgical instruments, for example, inserters, extenders, reducers, spreaders, distractors, blades, retractors, clamps, forceps, elevators and drills, which may be alternatively sized and dimensioned, and arranged as a kit.

In some embodiments, surgical system 10 includes an agent, which may be disposed, packed, coated or layered within, on or about the components and/or surfaces of surgical system 10. In some embodiments, the agent may include bone growth promoting material, for example, bone graft to enhance fixation of the components and/or surfaces of surgical system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   an arm connectable with a rack of a surgical distractor configured to be connected with vertebrae, the arm includes a receptacle configured for disposal of at least one blade; and
   at least one blade connected with the receptacle and being movable to space tissue adjacent the vertebrae, the at least one blade being intra-operatively translatable relative to the receptacle along a longitudinal axis of the receptacle, wherein the at least one blade includes a rail and the receptacle defines a longitudinal slot such that the rail is movable in the slot; and
   the arm comprising a support connected to the receptacle and a sleeve connected to the rack, the support being translatable relative to and within the sleeve such that the receptacle and the blade are reciprocally movable in a direction transverse to a length of the rack; and
   wherein the arm comprises a pivot housing at which the receptacle is rotatable about an axis extending substantially parallel to the rack.

2. A surgical instrument as recited in claim 1, wherein the at least one blade is intraoperatively rotatable relative to the longitudinal axis of the receptacle.

3. A surgical instrument as recited in claim 1, wherein the receptacle has a wall that defines a longitudinal groove for movable disposal of the at least one blade.

4. A surgical instrument as recited in claim 1, wherein the at least one blade is selectively fixable in a position relative to the surgical distractor.

5. A surgical instrument as recited in claim 1, wherein the at least one blade and the arm include a ratchet.

6. A surgical instrument as recited in claim 1, wherein the at least one blade is frictionally engageable with the receptacle to selectively fix the at least one blade in a position.

7. A surgical instrument as recited in claim 1, wherein the receptacle having a plurality of openings and the at least one blade having at least one projection disposable with a selected opening of the plurality of openings to lock the at least one blade in a selected position.

8. A surgical instrument as recited in claim 7, wherein the at least one projection is biased to a locking orientation.

9. A surgical instrument as recited in claim 1, wherein the support and the sleeve include a ratchet.

10. A surgical instrument as recited in claim 1, wherein the support includes a lock engageable with the receptacle.

11. A surgical instrument as recited in claim 10, wherein the lock is biased to a locking orientation.

12. A surgical instrument as recited in claim 1, wherein the at least one blade includes only one blade.

13. A surgical instrument as recited in claim 1, wherein the receptacle is configured for disposal of at least one blade and is selectively rotatable to a fixed position relative to the surgical distractor.

14. A surgical system comprising:
   a first implant support and a second implant support, the implant supports being engaged with bone fasteners configured to be fixed with vertebrae;
   a surgical distractor having a rack and being engageable with the implant supports;
   a surgical retractor having an arm connectable with the rack and at least one blade connected with a receptacle of the arm, the at least one blade being intra-operatively translatable and rotatable relative to the receptacle about a longitudinal axis of the receptacle to space tissue adjacent the vertebrae, wherein the receptacle comprises a plurality of openings and the at least one blade comprises at least one projection disposable with a selected opening of the plurality of openings to lock the at least one blade in a selected position and the at least one projection is biased to a locking orientation; and
   a locking tool engageable with the implant supports in a configuration to resist movement of the bone fasteners relative to the vertebrae;
   the arm comprising a support connected to the receptacle and a sleeve connected to the rack, the support being translatable relative to and within the sleeve such that the blade is reciprocally movable in a direction transverse to the rack; and
   a position of the arm being adjustable along a length of the rack between the first implant support and the second implant support of the surgical distractor independent of a position of the implant supports of the surgical distractor.

15. A surgical system as recited in claim 14, wherein the at least one blade includes only one blade.

16. A surgical distractor comprising:
   a rack extending in a first direction;
   an arm associated with the rack and comprising a longitudinal axis, wherein the arm comprises a receptacle configured for disposal of at least one blade;
   at least one blade, wherein the at least one blade is disposed at least partially within the receptacle and extends parallel to the longitudinal axis, the at least one blade being movable and operable to space tissue;
   the at least one blade being intra-operatively translatable and comprises a rail and the receptacle comprises a slot to receive the rail; and
   wherein the arm is connected to the rack by a support and a sleeve, the support being translatable within the sleeve such that the receptacle and blade are reciprocally movable in a direction substantially perpendicular to the first direction; and
   wherein the arm is rotatable about an axis extending parallel to the first direction.

17. A surgical system as recited in claim 1 wherein a position of the member is adjustable along a length of the rack independent of a position of the implant supports of the surgical distractor.

18. A surgical system as recited in claim 14, wherein the receptacle is pivotally connected to the support at a pivot point; the receptacle and the blade rotatable about an axis extending substantially parallel to the rack and that is coincident with the pivot point.

19. A surgical system as recited in claim 17, wherein the receptacle is connected to a pivot housing disposed on a distal end of the support.

* * * * *